United States Patent [19]

Grollier et al.

[11] 4,438,095

[45] Mar. 20, 1984

[54] NEW COSMETIC COMPOSITIONS FOR HAIR OR SKIN CONDITIONING, AND THE APPLICATION THEREOF

[75] Inventors: Jean-Francois Grollier, Paris; Josiane Allec, Pierrefitte, both of France

[73] Assignee: Societe Anonyme dite: L'Oreal, Paris, France

[21] Appl. No.: 244,313

[22] Filed: Mar. 16, 1981

[30] Foreign Application Priority Data

Mar. 18, 1980 [FR] France ................................. 80 05985

[51] Int. Cl.³ ...................... A45D 19/00; A61K 7/06; A61K 31/74; A61K 47/00
[52] U.S. Cl. .......................................... 424/70; 132/7; 424/78; 424/358; 424/365
[58] Field of Search .......................... 424/70, 358, 365; 132/7

[56] References Cited

U.S. PATENT DOCUMENTS

| 3,660,561 | 5/1972 | Shepherd et al. | 424/47 |
| 3,954,960 | 5/1976 | Valan | 424/47 |
| 4,189,468 | 2/1980 | Vanlerberghe | 424/71 |
| 4,240,450 | 12/1980 | Grollier et al. | 424/DIG. 1 |

Primary Examiner—Dale R. Ore
Attorney, Agent, or Firm—Cushman, Darby & Cushman

[57] ABSTRACT

The subject of this invention is a cosmetic composition for the conditioning of the skin or hair, characterized by the fact that it is made up of two separate liquid phases, the first phase being an aqueous phase in which at least on cationic polymer is dissolved, and by the fact that the said composition contains no detergent agents or foaming agents.

6 Claims, No Drawings

NEW COSMETIC COMPOSITIONS FOR HAIR OR SKIN CONDITIONING, AND THE APPLICATION THEREOF

The subject of this invention is new cosmetic compositions for hair or skin conditioning, and the application thereof.

Oils and mixtures of oils have always been used for the conditioning of the hair, in particular dry or sensitive hair, i.e., hair which has been damaged by exposure to an unfavorable environment (sun, sea water, etc.) or by treatments such as permanents, hair colorings or bleaching.

Similarly, oily cosmetic compositions have been used for skin conditioning, i.e., to make dry, wrinkled or rough skin more flexible and smooth to the touch.

Despite their ease of application and impregnation, after rinsing and/or shampooing oils provide the hair with but a slight degree of the properties sought, namely an appreciable softness to the touch, a shining appearance and a protective effect with respect to the environment. In like manner, the use of a purely oil-based composition for the skin is not fully satisfactory particularly because of problems with uniform spreading, with the resulting greasy appearance, and with the unpleasant "greasiness" to the touch.

This explains why, for some time now, the use of oil-based products has little by little given way to that of other products which are more effective for the conditioning and protection of sensitive hair and the skin. These new products, used in modern cosmetic compositions, include inter alia polymers of the polyamine, polyaminoamide or quaternary polyammonium types, with the amine or ammonium groups being part of the ammonium chain or being bonded to it. Such polymers, and their use in cosmetic compositions, have been described in numerous publications, and many cosmetology specialists have grouped these polymers together in a class generally designated by the term "cationic polymers." Although the effects of these cationic polymers may vary, specialists have recognized that they all share, albeit to different degrees, the property of adhering to the skin and the hair and facilitating the untangling of wet hair.

However, efforts to incorporate the cationic polymers in oils have not made it possible to produce effective cosmetic compositions. In some cases, it was impossible to incorporate the cationic polymers in the oils because the polymers in question could not be isolated in the dry state and were available only in aqueous solution, or because the polymers were not soluble in oils. In other cases, it was possible to incorporate the polymers in oils, but then the effectiveness of the polymers was very slight because their characteristic adherence to the skin or hair was inhibited in the oily medium.

Another possibility for combining the effects of oils and cationic polymers was first to apply an aqueous solution of a cationic polymer, and then to apply an oil. However, these attempts likewise failed, either because the amount of water involved (aqueous solution of cationic polymer) was too small and it was not possible to distribute the polymer uniformly over the entire head of hair, or because the amount of water was sufficient for proper distribution over the hair but caused the oil to be spread unevenly over the wet hair. The oil was similarly poorly spread over wet skin.

It has now been discovered that it is possible to combine the cosmetic effects of oils and cationic polymers thanks to a special nondetergent, nonfoaming composition which is the subject of this invention.

The subject of this invention is a cosmetic composition for the conditioning of the skin or hair, characterized by the fact that it is made up of two separate liquid phases, the first phase being an aqueous phase in which at least one cationic polymer is dissolved, and by the fact that the said composition contains no detergent agents or foaming agents.

The oils which are usable in the compositions covered by this application are, generally speaking, any of those oils usable in cosmetic products for the skin or for the hair.

These are, inter alia, the vegetable oils such as, for example, almond oil, peanut oil, wheat germ oil, lineseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grape seed oil, sunflower seed oil, etc.

The oily phase of the compositions according to the invention may also contain animal oils, such as whale oil, lard, oil from horses' hooves, tuna, horses, seal oil, egg oil, sheep oil, turtle oil. halibut liver, marmot liver or cod liver oil, neat's-foot oil, tallow, etc.

The oily phase may also contain a synthetic oil, preferably made up of carbon, hydrogen and oxygen, such as the ethers or esters of glycol or glycerol described in French Patent Nos. 74 09657, 75 24656, 75 24657 and 75 24658.

The oil phase may likewise contain a mineral oil such as vaseline.

It is preferable for the oily phase to contain no silicon oils.

In general, it is preferred to use a vegetable oil, perhaps mixed with an animal oil and or a mineral and/or synthetic oil as defined above.

In this preferred procedure, the proportion of vegetable oil generally ranges from 25% to 100% in volume terms with respect to the total volume of the oily phase, with any additional amount being made up of one or several animal, synthetic and/or mineral oils.

As indicated above, the cationic polymers which are usable in cosmetic products for hair constitute a class which is well known to cosmetology specialists. Such cationic polymers are the polycationic products described inter alia in French patents and French patent application Nos. 2.077.143, 1.492.597, 2.162.025, 2.280.361, 2.252.840, 2.368.508, 1.583.363, 2.080.759, 2.190.406, 2.320.330, 2.270.846, 76 20261, 2.336.434, 2 413 907 and 2.189.434; and in U.S. Pat. Nos. 3,227,615, 2,961,347, 2,273,780, 2,375,853, 2,388,614, 2,454,547, 3,206,462, 2,261,002, 2,271,378, 3,874,870, 4,001,432, 3,929,990, 3,996,904, 4,005,193, 4,025,617, 4,025,627, 4,025,653, 4,026,945, 3,589,978, 4,031,307 and 4,027,020.

The cationic polymers used in the composition according to the invention are polymers of the polyamine, polyaminoamide or quaternary polyammonium type, with the amine or ammonium grouping constituting part of the polymer chain or being bonded thereto.

Polymers of this type which are usable in accodance with the invention are, inter alia:

1. vinyl-pyrrolidone-acrylate or methacrylate copolymers of aminoalcohol (whether or not quaternized), such as those sold under the tradename Gafquat by the GAF Corporation, e.g., "copolymer 845,", "Gafquat 734 or 755," described inter alia in greater detail in French patent No. 2.077.143;

2. derivatives of cellulose ethers entailing quarternary ammonium groupings, such as those described in French patent no. 1.492.597, and, in particular, the polymers sold under the designations JR, such as JR 125, JR 400, JR 30 M, and LR, such as LR 500 and LR 30 M, by the Union Carbide Corporation, and derivatives of cationic cellulose such as CELQUAT L 200 and CELQUAT L 60 and H 100 sold by the National Starch Company;

3. cationic polysaccharides such as those described in U.S. Pat. Nos. 3,589,978 and 4,031,307 and, in particular, Jaguar C 13 S sold by the MEYHALL and CELANESE companies;

4. the cationic polymers chosen from the group made up of:

(a) the polymers containing units following the formula —A—Z—A—Z— in which A designates a radical with two amine functions, preferably

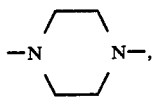

and Z designates the symbol B or B'; B and B', which may be identical or different, designate a bivalent radical which is an alkylene radical with a straight or branched chain, consisting in up to 7 consecutive carbon atoms in the main chain which are or are not replaced by hydroxyl groupings and may in addition entail atoms of oxygen, nitrogen, sulfur, 1 to 3 aromatic cycles and or heterocycles; the oxygen atoms, nitrogen atoms or sulfur atoms are present in the form of ether or thioether groupings, sulfoxides, sulfone, sulfonium, amine, alkyamine, alkenylamine, benzylamine, amine oxide, quarternary ammonium, amide, imide, alcohol, ester and/or urethane; these polymers and the procedure for their preparation are described in French patent No. 2.162.025;

(b) the polymers containing units with the formula: —A—$Z_1$—A—$Z_1$— in which A designates a radical containing two amine functions, and prefeably

and $Z_1$ designates the symbol $B_1$ or $B'_1$ and signifies at least once the symbol $B'_1$; $B_1$ designates a bivalent radical, which is an alkylene or hydroxyalkylene radical with a straight or branched chain having as many as seven consecutive carbon atoms in the principal chain, $B'_1$ is a bivalent radical which is an alkylene radical having a straight or branched chain having up to seven consecutive carbon atoms in the principal chain, which is or is not substituted by one or several hydroxyl radicals and interrupted by one or several nitrogen atoms, the nitrogen atom being substituted by an alkyl chain with possible one to 4 atoms of carbon, preferably 4, possibly interrupted by an oxygen atom and perhaps containing one or several hydroxyl functions; these polymers and the procedure for their preparation are described in French patent No. 2.280.361;

(c) the quaternary ammonium salts and the oxidation products of the polymers with formulas indicated sub (a) and (b) above.

5. The reticulated polyaminoamides, perhaps alkylated, from the group formed by at least one water-soluble reticulated polymer obtained by the reticulation of a polyaminopolyamide (A) prepared by polycondensation of an acid compound with a polyamine, the acid compound being selected from among: (i) the dicarboxylic organic acids, (ii) the mono- and dicarboxylic aliphatic acids with double ethylene bonds, (iii) the esters of the above acids, preferably the esters of lesser alkanols having from 1 to 6 carbon atoms, and (iv) mixtures of these compounds. The polyamine is selected from among the bis-primary, mono- or bis secondary polyalkylene-polyamines. 0 to 40 moles % of this polyamine may be replaced by a bis primary amine, preferably piperazine, and 0 to 20 moles % may be replaced by hexamethylenediamine. Reticulation is effected by means of a reticulating agent (B) selected from the epihalohydrines, the diepoxides, the dianhydrides, the unsaturated anhydrides, the unsaturated bis derivatives, and the reticulation is characterized by the fact that it is carried out by means of 0.025 to 0.35 mole of reticulating agent per amine grouping of the polyaminopolyamide (A), and generally from 0.025 to about 0.2 mole, in particular 0.025 to about 0.1 mole of reticulating agent per amine group of the polyaminopolyamide (A). These polymers and their preparation are described in greater detail in French patent application No. 2.252.840.

Also usable are, on the one hand, the A polyaminoamides and, on the other hand, the water-soluble reticulated polyaminoamides obtained by the reticulation of a polyaminoamide (A described above) by means of a reticulating agent selected from the group formed by:

(I) the compounds selected from the group formed of (1) the bis halohydrines, (2) the bis azetidiniums, (3) the bis haloalkyls of diamines, and (4) the bis halogenates of alkyl;

(II) the oligomers obtained by reaction of a compound (a') selected from the group formed by (1) the bis halohydrines, (2) the bis azetidiniums, (3) the bis haloalkyls of diamines, (4) the bis halogenates of alkyls, (5) the epihalohydrines, (6) the diepoxides, and (7) the unsaturated bis derivatives, with a compound (b') which is a bifunctional compound which is reactive with respect to compound (a').

(III) the product of quaternization of a compound selected from among the group mde of the (a') compounds and the (II) oligomers and containing one or several tertiary amine groups which have been totally or partially alkylated with an alkylating agent (c) preferably selected from among the group made up of the chlorides, bromides, iodides, sulfates, methyl or ethyl mesylates or tosylates, propylene oxide, and glycidol, with the reticulation carried out by means of 0.025 to 0.35 mole, in particular 0.025 to 0.2 mole and most particularly 0.025 to 0.1 mole of reticulating agent per amine group of the polyaminoamide.

These reticulating agents and these polymers, as well as the procedure for their preparation, are described in French patent application No. 2.368.508.

6. The derivatives of the water-soluble polyaminoamides resulting from the condensation of polyalkylene polyamines with polycarboxylic acids followed by alkylation by means of bifunctional agents such as the copolymers of adipic-dialkylaminohydroxyalkyl-dialkylene triamine acid, in which the alkyl radical contains 1 to 4 carbon atoms and designates preferably methyl, ethyl, propyl, as described in French patent No. 1.583.363.

Among these derivatives, mention may be made of the adipicdimethylaminohydroxy-propyl-diethylene-triamine acid copolymers sold under the trade name Cartaretine F, F$_4$ or F$_8$ by the SANDOZ company.

7. The polymers obtained by the reaction of a polyalkylene polyamine containing two primary amine groups and at least one secondary amine group with a dicarboxylic acid selected from among diglycolic acid and saturated aliphatic dicarboxylic acids with 3 to 8 carbon atoms. The molar ratio between the polyalkylene polyamine and the dicarboxylic acid is between 0.8 to 1 and 1.4 to 1; the resulting polyamide is induced to react with epichlorhydrine in a molar ratio of epichlorhydrine with respect to the secondary amine group of the polyamide of between 0.5 to 1 and 1.8 to 1; references in U.S. Pat. Nos. 3,227,615 and 2,961,347.

Polymers of this type include those sold under the trade name HERCOSETT 57 by the Hercules Company, Inc., and have a viscosity of 30 cps at 25° C. at 10% in aqueous solution, and under the trade name PD 170 or DELSETTE 101 by the Hercules company in the case of the adipic acid copolymer, epoxypropyl diethylene-triamine.

8. The water-soluble cyclopolymers with a molecular weight of 20,000 to 3,000,000 such as the homopolymers entailing as the principal constituent of the chain, units which correspond to formula (II) or II'):

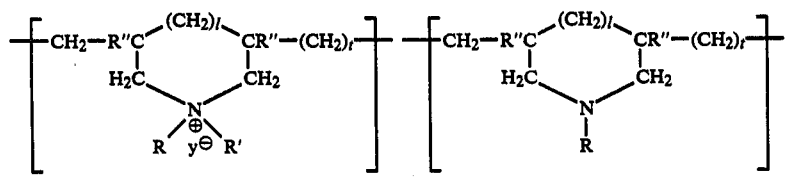

in which l and t are equal to 0 or 1, t=1 when l=0 and t=0 when l=1, R" designates hydrogen or methyl, R and R' designate, independently of one another, an alkyl group having 1 to 22 carbon atoms, a hydroxyalkyl group in which the alkyl group preferably has 1 to 5 carbon atoms, a lower amidoalkyl group, and where R and R' may designate, in conjunction with nitrogen atom to which they are attached, heterocyclic groups such as piperidinyl or morpholinyl, as well as the copolymers entailing units with formula II or II' and, preferably, units derived from acrylamide or from acrylamide diacetone, and $Y^\ominus$ is an anion, such as bromide, chloride, acetate, borate, citrate, bisulfate, bisulfite, sulfate, or phosphate.

Among the quaternary ammonium polymers of the type defined above, mention may be made of the homopolymers of dimethyl diallyl ammonium chloride sold under the trade name MERQUAT 100, with a molecular weight of less than 100,000, and of the copolymer of dimethyl diallyl ammonium chloride and acrylamide with a molecular weight in excess of 500,00 and sold under the trade name of MERQUAT 550 by the MERCK company.

These polymers are described in French Patent No. 2.080.759 and its amendment certificate No. 2.190.406.

9. The water-soluble quaternary polyammoniums containing recurrent units of the formula:

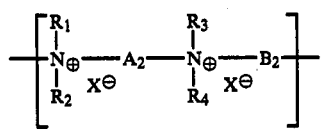

in which $R_1$ and $R_2$, $R_3$ and $R_4$, equal or different, represent aliphatic radicals, or lower hydroxyaliphatics, having a maximum of 4 carbon atoms, with it possible for one of them, however, to represent an aliphatic radical containing 5 to 16 carbon atoms, an alicyclic radical or an arylaliphatic radical on condition that, in such a case, the total number of carbon atoms in groups $A_2$ and $B_2$ is equal to not more than 12, or if $R_1$, $R_2$, $R_3$ and $R_4$, taken together or separately, with the nitrogen atoms to which they are attached constitute heterocycles perhaps containing a second heteroatom other than nitrogen, or if $R_1$, $R_2$, $R_3$ and $R_4$ represent a grouping:

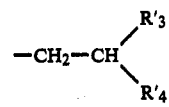

in which $R'_3$ designates hydrogen or a lower alkyl and $R'_4$ designates one of the following groups: -CN,

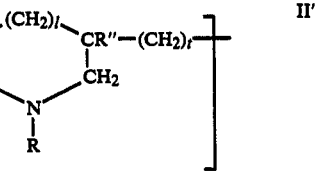

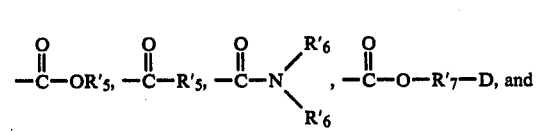

with $R'_5$ designating lower alkyl, $R'_6$ designating hydrogen or a lower alkyl, $R'_7$ designating alkylene, D designating a quaternary ammonium group, and $A_2$ and $B_2$ represent divalent groups, e.g., polymethylenic groups containing 2 to 20 carbon atoms, which may be linear or branched, saturated or unsaturated, and may contain, within the principal chain, one or more aromatic cycle(s) such as the group

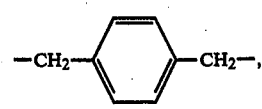

one or more groups $-(CH_2)_n-Y_1-(C_2)_n-$  $Y_1$ designating O, S, SO, $SO_2$, $-S-S-$,

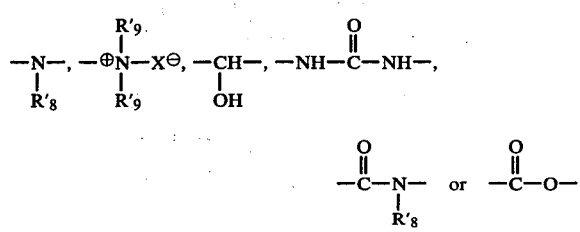

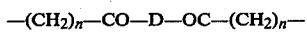

with $X^\ominus$ designating an anion derived from a mineral or organic acid, n being 2 or 3, $R'_8$ designating hydrogen or lower alkyl, $R'_9$ designating lower alkyl, or with $A_2$, and $R_1$ and $R_3$ form, with the two nitrogen atoms to which they are attached, a piperazine cycle; in addition, if $A_2$ designates an alkylene radical or hydroxyalkylene, whether liner or branched, saturated or unsaturated, $B_2$ may also designate a group:

$$-(CH_2)_n-CO-D-OC-(CH_2)_n-$$

in which D designates (a) a glycol residue with the formula $-O-Z-O-$ where Z designates a linear or branched hydrocarbon radical or a group with the formulas:

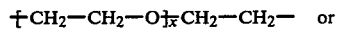

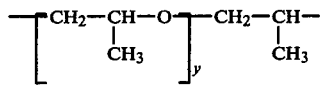

where x and y designate an integer from 1 to 4, representing a defined and unique degree of polymerization, or any number from 1 to 4 representing an average degree of polymerization;

(b) a secondary diamine bis residue such as a piperazine derivative with the formula:

(c) a primary diamine bis residue with the formula:

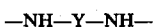

where Y designates a linear or branched hydrocarbon radical or the bivalent radical

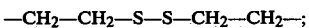

(d) a urylene group with the formula $-NH-CO-NH-$: and $X^\ominus$ is an anion such as chloride or bromide.

These polymers have a molecular mass which is generally in the range of 1,000 to 100,000.

Polymers of this type are described, in particular, in French patent Nos. 2.320.330, 2.270.846, French patent application Nos. 76 20261 and 2.336.434, and U.S. Pat. Nos. 2,273,780, 2,375,853, 2,388,614, 2,454,547, 3,206,462, 2,261,002, 2,271,378.

Other polymers of this type are described in U.S. Pat. Nos. 3,874,870, 4,001,432, 3,929,990, 3,966,904, 4,005,193, 4,025,617, 4,025,627, 4,025,653, 4,026,945 and 4,027,020.

10. Homopolymers or copolymers derived from acrylic or methacrylic acid and containing the unit:

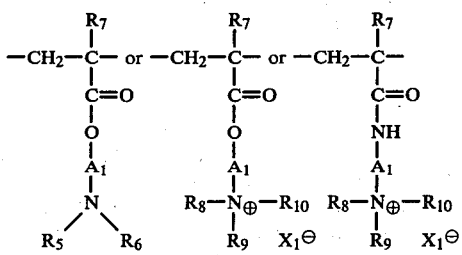

in which $R_7$ is H or $CH_3$, $A_1$ is a linear or branched alkyl group with 1 to 6 carbon atoms or a hydroxylalkyl group with 1 to 4 carbon atoms, $R_8$, $R_9$, $R_{10}$, identical or different, represent an alkyl group with 1 to 18 atoms or benzyl, $R_5$ and $R_6$ represent H or alkyl with 1 to 6 carbon atoms, and $X_1$ designates halogen, such as chloride, bromide or methosulfate.

The usable comonomer(s) belong to the family of acrylamide, methacrylamide, diacetone acrylamide, acrylamide and methacrylamide with lower alkyls replacing the nitrogen, alkyl esters of acrylic and methacrylic acids, vinyl pyrrolidone, and vinylic esters.

By way of example, reference may be made to:

the copolymer of acrylamide and of beta methacryloyloxyethyl trimethylammonium methosulfate, sold under the trade names of Reten 205. 210, 220 and 240 by the Hercules company, the copolymers of ethyl methacrylate, oleyl methacrylate, beta methacryloyloxyethyldiethyl methylammonium methosulfate, listed under references with the name Quaternium 38 in the Cosmetic Ingredient Dictionary, the copolymer of ethyl methacrylate, abietyl methacrylate and beta-methacryloyloxyethyldiethyl methylammonium methosulfate listed in references under the name Quaternium 37 in the Cosmetic Ingredient Dictionary, the polymer of beta-methacryloyloxyethyl trimethylammonium bromide listed in references under the name Quaternium 49 in the Cosmetic Ingredient Dictionary, the copolymer of beta methacryloyloxyethyl trimethylammonium methosulfate and beta methacryloyloxyethyl stearyldimethylammonium methosulfate listed in references under the name of Quaternium 42 in the Cosmetic Ingredient Dictionary, the copolymer of aminoehylacrylate phosphate/acrylate sold under the trade name Catrex by the National Starch company, the grafted and reticulated cationic copolymers with a molecular weight of 10,000 to 1,000,000, and preferably from 15,000 to 500,000, resulting from the copolymerization of:

(a) at least one cosmetic monomer,
(b) dimethylaminoethyl methacrylate,
(c) polyethylene glycol, and
(d) a polyunsaturated reticulating agent described in French patent No. 2.189.434.

The reticulating agent is selected from the group made up of ethylene glycol dimethacrylate, the diallyl phtalates, the divinylbenzenes, tetraallyloxyethane, and the polyallylsucroses.

The cosmetic monomer may be any of a wide range of types, e.g., a vinylic ester of an acid with from 2 to 18 carbon atoms, an allylic ester or methallylic ester of an acid with from 2 to 18 carbon atoms, an acrylate or methacrylate of a saturated alcohol with from 1 to 18 carbon atoms, a vinylether alkyl whose alkyl radical has 2 to 18 carbon atoms, an olefin with from 4 to 18 carbon atoms, a heterocyclic vinylic derivative, a maleate of dialkyl or of N,N-dialkylaminoalkyl whose alkyl radicals have 1 to 3 carbon atoms, or an anhydride of an unsaturated acid.

Other usable cationic polymers include, for example, the polyalkylene imines, in particular the polyethylenimines, polymers containing vinylpyridine or vinylpyridinium units in the chain, condensates of polyamines and of epichlorhydrine, quaternary polyureylenes, and chitine derivatives.

In the compositions according to the invention, the proportion of the aqueous phase preferably ranges from 2 to 50% in volume terms with respect to the total volume of the composition.

The cationic polymer which is dissolved in the aqueous phase is present in the composition according to the invention in an amount ranging from 0.2 to 50% by weight in relation to the total weight of the composition.

In addition to the cationic polymer, the aqueous phase may contain, in the dissolved state, inter alia preservatives, thickening agents, coloring agents, and/or hydrosoluble solvents such as alcohols (ethanol in particular). These solvents, when present, represent a maximum of 50% by volume with respect to the total volume of the aqueous phase.

The oily phase may contain, inter alia, anti-oxidizing agents, coloring agents and/or perfumes in the dissolved state. The compositions covered by this application are free of detergent and foaming agents. More generally, they contain no anionic tensioactives and amphoteres; most frequently, the compositions covered by this application are free of all tensio-active agents. However, in some cases, they may contain a slight quantity (less than 3% by weight) of cationic tensio-active present as a cosmetic agent. Indeed, it is known that the cationic tensio-actives, in being deposited on the hair or skin, have the effect of conditioning it.

Also the subject of the invention is the application of the two-phase composition described above, i.e. its use in the treatment and conditioning of hair, particularly dry or sensitive hair, and in the treatment and conditioning of the skin, particularly dry, wrinkled, rough or hard skin.

In the case of hair conditioning, this use is effected in accordance with a method characterized by the fact that the composition in question is shaken to disperse the aqueous phase in the oily phase, that from 5 to 40 cubic centimeters of the shaken composition are applied to the hair and allowed to act for at least five minutes, and then that the hair is rinsed. If desired, the hair may then be shampooed, preferably with an anionic shampoo.

Preferably, the composition is allowed to act for at least five minutes. It is, of course, possible to allow it to act for several hours.

Generally speaking, this conditioning of the hair may be carried out before or after shampooing, coloring, bleaching, a permanent wave, or straightening.

In the case of skin conditioning, the composition is shaken in order to disperse the aqueous phase in the oily phase, and the shaken composition is then spread over the skin, massaging it if desired. Excess composition may be removed with an absorbent wiper (cotton or paper tissue), but, unlike the situation for the hair, the composition is not rinsed off. Preferably, the composition is applied to skin which has been freshly washed.

The following examples illustrate the invention, without, however, restricting it.

In these examples, the symbols designating the cationic polymers have the following meanings:

Polymer $P_1$: Polymer made of units of the formula:

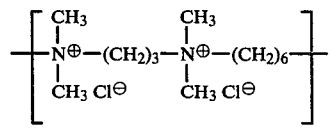

which can be prepared as described in French Patent Nos. 2.270.846 and 2.333.012.

JR 400: Polymer of hydroxyethylcellulose and epichlorhydrine quaternized with trimethylamine, having a viscosity of 400 cps, sold by the Union Carbide Corporation.

Merquat 100: Homopolymer of dimethyldiallyl ammonium chloride with a molecular weight of less than 100,000, sold by Merck & Co.

CARTARETINE F.4: Adipic acid/dimethylaminohydroxypropyl diethylene triamine copolymer, sold by the Sandoz Company.

Polymer $P_2$: Polycondensate of adipic acid and of diethylene triamine in equimolecular amounts, reticulated with epichlorhydrine (11 moles of epichlorhydrine per 100 amine groups)) described in French Patent No. 2.252.840.

EXAMPLE 1

Oily and aqueous phases with the following compostiions are prepared:

Oily phase

Corn oil: 20 cc
Antioxidant q.s.*
Perfume q.s.
Coloring q.s.
Sunflower oil q.s.p: 100 cc
*q.s.=quantum sufficit, as much as suffices.

Aqueous phase

Polymer $P_1$: 5 g (A.I.)*
Preservative q.s.
Coloring q.s.
Water q.s.p.: 100 cc
*A.I.=active ingredient.

The two-phase composition is obtained by combining 2cm³ of the aqueous phase with 18 cm³ of the oily phase.

After shaking, the composition is applied on dry or sensitive hair. After a waiting time of 5 minutes to 4 hours, but preferably after 15 minutes, rinsing is carried out, followed by shampooing.

The wet hair may be untangled easily. The hair when dry is soft, shiny and full of body.

Comparable results are obtained by using the following compositions:

EXAMPLE 2

A mixture of 16 cc of oily phase and 4 cc of aqueous phase with the following compositions:

Oily phase

Avocado oil: 10 cc
Anti-oxidant q.s.
Perfume q.s.
Coloring q.s.
Colza oil q.s.p.: 100 cc Aqueous phase Polymer $P_1$: 1.5 g (A.I.)
JR 400: 1 g (A.I.)
Preservative q.s.
Coloring q.s.
Water q.s.p.: 100 cc

EXAMPLE 3

A mixture of 18 cc of oily phase and 2 cc of aqueous phase with the following compositions:

Oily phase

Castor oil: 5 cc
Anti-oxidant q.s.
Perfume q.s.
Coloring q.s.
Soybean oil q.s.p. 100 cc Aqueous phase Merquat 100: 3 g (A.I.)
Cartaretine $F_4$: 5 g (A.I.)
Preservative q.s.
Coloring q.s.
Water q.s.p.: 100 cc

EXAMPLE 4

A mixture of 16 cc of oily phase and 4 cc of aqueous phase with the following compositions:

Oily phase
Identical to that of Example 3

Aqueous phase

Polymer $P_1$: 1.5 g (A.I.)
Polymer $P_2$: 3.5 g (A.I.)
Ethyl alcohol q.s.p.: 50°
Preservative q.s.
Coloring q.s.
Water q.s.p.: 100 cc

EXAMPLE 5

A mixture of 16 cc of oily phase and 4 cc of aqueous phase with the following compositions:

Oily phase

Linseed oil: 1 cc
Anti-oxidant q.s.
Perfume q.s.
Coloring q.s.
Sweet almond oil q.s.p.: 100 cc Aqueous phase Polymer $P_1$: 1.5 g (A.I.)
Polymer $P_2$: 3.5 g (A.I.)
Preservative q.s.
Coloring q.s.
Water q.s.p.: 100 cc

EXAMPLE 6

A mixture of 10 cc of oily phase and 10 cc of aqueous phase with the following compositions:

Oily Phase

Jojoba oil: 20 cc
Anti-oxidant q.s.
Perfume q.s.
Coloring q.s.
Sesame oil q.s.p.: 100 cc Aqueous phase Identical to that of Example 3

EXAMPLE 7

A mixture of 10 cc of oily phase and 10 cc of aqueous phase with the following compositions:

Oily phase

Peach pit oil: 10 cc
Vaseline oil: 30 cc
Preservative q.s.
Perfume q.s.
Coloring q.s.
Olive oil q.s.p.: 100 cc Aqueous phase Identical to that of Example 1

EXAMPLE 8

A mixture of 18 cc of oily phase and 2 cc of aqueous phase with the following compositions:

Oily phase
Identical to that of Example 7

Aqueous phase

Merquat 100: 3 g (A.I.)
Cartaretine $F_4$: 5 g (A.I.)
Ethyl alcohol q.s.p.: 25°
Preservative q.s.
Coloring q.s.
Water q.s.p.: 100 cc

EXAMPLE 9

A mixture of 16 cc of oily phase and 4 cc of aqueous phase with the following compositions:

Oily phase

Horse fat: 25 cc
Anti-oxidant q.s.
Perfume q.s.
Coloring q.s.
Wheat germ oil q.s.p.: 100 cc Aqueous phase Identical to that of Example 5

EXAMPLE 10

A mixture of 19.5 cc of oily phase and 0.5 cc of aqeuous phase with the following compositions:

Oily phase
Identical to that of Example 2

Aqeuous phase

Polymer $P_1$: 60 g (A.I.)

Preservative q.s.
Coloring q.s.
Water q.s.p.: 100 cc

EXAMPLE 11

A mixture of 10 cc of oily phase and 10 cc of aqueous phase with the following compositions:

Oily phase

Identical to that of Example 3

Aqueous phase

Merquat 100: 0.3 g (A.I.)
Cartaretine F$_4$: 0.3 g (A.I.)
Preservative q.s.
Coloring q.s.
Water q.s.p.: 100 cc

EXAMPLE 12

A mixture of 16 cc of oily phase and 4 cc of aqueous phase with the following compositions:

Oily phase

Anti-oxidant q.s.
Perfume q.s.
Coloring q.s.
Jojoba oil q.s.p.: 100 cc

Aqueous phase

Merquat 100: 2 g (A.I.)
Preservative q.s.
Coloring q.s.
Water q.s.p.: 100 cc

After shaking, the composition is applied on the skin, giving it flexibility and softness. Similar results are obtained by applying the composition of Example 2 to the skin.

We claim:

1. A non-detergent, non-foaming cosmetic composition for conditioning the hair or skin consisting essentially of two separate liquid phases for admixture at the time of use, one of said liquid phases comprising an aqueous phase containing a soluble cationic polymer and the other of said phases comprising an oily phase, said aqueous phase being present in an amount ranging from 2–50 volume percent of said composition the balance being said oily phase, said soluble cationic polymer being present in an amount ranging from 0.2 to 50 weight percent based on the total weight of said composition and said oily phase comprising 25 to 100 volume percent of a vegetable oil.

2. The cosmetic composition of claim 1 wherein said cationic polymer is
   (1) a quaternized or non-quaternized vinyl pyrrolidone acrylate or a vinyl pyrrolidone methacrylate copolymer of an aminoalcohol,
   (2) a quaternary derivative of a cellulose ether,
   (3) a cationic polysaccharide,
   (4) a cationic polymer (a) having recurring units of the formula —A—Z—A—Z—, wherein A represents a radical having two amino groups and Z represents the symbol B or B', which symbols may be identical or different and represent a straight or branched chain alkylene radical having 1-7 carbon atoms in the main chain, said alkylene radical being unsubstituted or substituted by hydroxyl groups and which can additionally contain chain oxygen, nitrogen or sulfur atoms and 1 to 3 aromatic rings or heterocyclic rings; or (b) having recurring units of the formula —A—Z$_1$—A—Z$_1$— wherein A is as defined above and Z$_1$ represents the symbol B$_1$ or B'$_1$ such that at least one Z$_1$ represents B'$_1$, B$_1$ being an alkylene or hydroxyalkylene radical having 1-7 carbon atoms in the main chain and B'$_1$ being an alkylene radical having 1-7 carbon atoms in the main chain which is unsubstituted or substituted by one or more hydroxyl radicals and containing one or more chain nitrogen atoms which are substituted by an alkyl radical which optionally contains a chain oxygen and one or more hydroxyl groups, or (c) being the quaternary ammonium salts and oxidation products of cationic polymers (a) and (b) defined above,
   (5) a crosslinked polyaminoamide, optionally alkylated, said polyamide prepared by polycondensation of an acid compound with a polyamine, said acid compound being selected from the group consisting of (i) a dicarboxylic organic acid, (ii) an ethylenically unsaturated aliphatic mono- or dicarboxylic acid, (iii) an ester of (i) and (ii), and (iv) mixtures of (i), (ii) and (iii), said polyamine being selected from the group consisting of bis-primary and mono- or bis-secondary polyalkylene-polyamines, said polyamine being replaceable by a member selected from the group consisting of (1) 0–40 mole percent bis-primary amine and (2) 0–20 mole percent hexamethylene diamine, said crosslinking agent being selected from the group consisting of
   (a) an epihalohydrin,
   (b) a diepoxide,
   (c) a dianhydride,
   (d) an unsaturated anhydride,
   (e) a compound selected from the group consisting of a bis halohydrin, a bis azetidinium, a diamine bis haloalkyl and an alkyl bis halogenate,
   (f) an oligomer obtained by the reaction of a compound (a') selected from the group consisting of compounds (a), (b), and (e) defined above with a compound (b') which is a bi-functional compound reactive with said compound (a'), and
   (g) the quaternization product of the compound (a') and the oligomer (f), said product having one or more tertiary amine groups alkylated with an alkylating agent selected from the group consisting of methyl or ethyl chloride, bromide, iodide, sulfate, mesylate and tosylate, propylene oxide and glycidol,
   (6) a water-soluble polyaminoamide prepared by condensation of a polyalkylene polyamine with a polycarboxylic acid, the resulting condensate being alkylated by a bifunctional aget which is a copolymer of adipic acid-dialkylaminohydroxyalkyl-dialkylene triamine wherein the alkyl moieties contain 1-4 carbon atoms,
   (7) a polymer obtained by the reaction of a polyalkylene polyamine containing two primary amine groups and at least one secondary amine group with a dicarboxylic acid selected from the group consisting of diglycolic acid and a saturated aliphatic dicarboxylic acid having 3 to 8 carbon atoms, wherein the molar ratio between said polyalkylene polyamine and said dicarboxylic acid ranges from 0.8–1.4 to 1, so as to produce a polyamide, a resulting polyamide being reacted with epichlorohydrin in a molar ratio of epichlorohydrin to the secondary amine group of said polyamide ranging from 0.5–1.8 to 1;

(8) a water-soluble cyclopolymer, having a molecular weight ranging from 20,000 to 3,000,000, which is (a) a homopolymer having recurring units of the formula

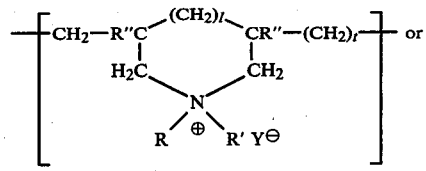
II

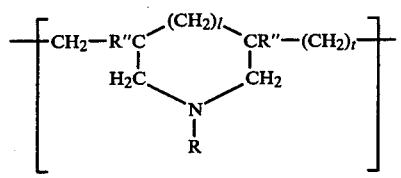
II' wherein l and t are equal to 0 or 1, with the proviso that t=1 when l=0 and t=0 when l=1, R" represents hydrogen or methyl, R and R' each independently represent alkyl having 1–22 carbon atoms, hydroxyalkyl having 1–5 carbon atoms or lower amidoalkyl, or R and R' together with the nitrogen atom to which they are attached form a heterocycle selected from the group consisting of piperdinyl and morpholinyl, or (b) a copolymer of units II or II' defined above, and $Y^{\ominus}$ is an anion selected from the group consisting of bromide, chloride, acetate, borate, citrate, bisulfate, bisulfite, sulfate and phosphate, (9) a water-soluble quaternary polyammonium containing recurring units of the formula

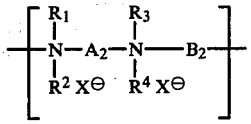

wherein $R_1$, $R_2$, $R_3$ and $R_4$ each independently represent an aliphatic radical, a lower hydroxyaliphatic radical having 1–4 carbon atoms, an alicyclic radical or an arylaliphatic radical with the proviso that the total number of carbon atoms in $A_2$ and $B_2$ is not greater than 12, or the pairs $R_1$, $R_2$ and $R_3$, $R_4$, each independently, together with the nitrogen atom to which they are attached form a heterocycle, or $R_1$, $R_2$, $R_3$, and $R_4$ independently represent a group of the formula

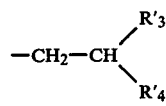

wherein $R'_3$ represents hydrogen or lower alkyl and $R'_4$ represents

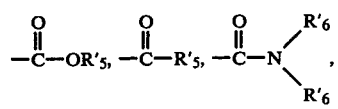

-continued
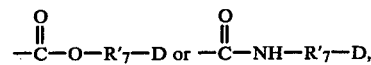

wherein $R'_5$ represents lower alkyl, $R'_6$ represents hydrogen or lower alkyl, $R'_7$ represents alkylene, D represents a quaternary ammonium group, and $A_2$ and $B_2$ each independently represent a linear or branch saturated or unsaturated polymethylene group containing 2 to 20 carbon atoms and which can contain in the main chain one or more aromatic groups of the formula

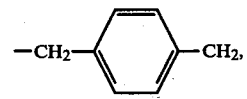

one or more groups of the formula $-(CH_2)_n-Y_1-(CH_2)_n-$ wherein $Y_1$ represents O, S, SO, $SO_2$, $-S-S-$,

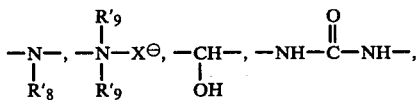

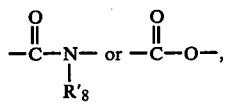

wherein $X^{\ominus}$ represents an anion derived from an organic or mineral acid, n is 2 or 3, $R'_8$ represents hydrogen or lower alkyl, $R'_9$ represents lower alkyl, or $A_2$, $R_1$ and $R_3$ together with the nitrogen atoms to which they are attached for a piperizine ring, or when $A_2$ represents alkylene or hydroxyalkylene $B_2$ can also represent $-(CH_2)_n-CO-D-OC-(CH_2)_n-$ wherein D represents (a) a glycol residue of the formula $-O-Z-O-$ wherein Z represents a linear or branched hydrocarbon radical or a group of the formula

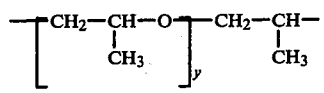

wherein x and y represent an integer from 1 to 4, (b) a bis-secondary diamine radical, (c) a radical of a bis-primary diamine of the formula $-NH-Y-NH-$ wherein Y represents a linear or branched hydrocarbon or a divalent radical $-CH_2-CH_2-S-S-CH_2-CH_2-$, or (d) a urylene group of the formula $-NH-CO-NH-$, and $X^{\ominus}$ is chloride or bromide;

(10) a homopolymer or copolymer derived from acrylic acid or methacrylic acid, containing units of the formula

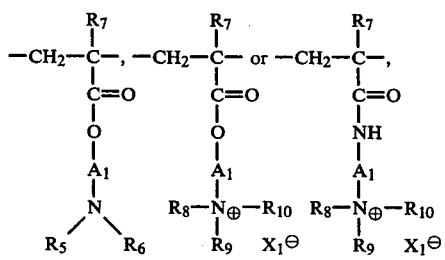

wherein $R_7$ is hydrogen or $CH_3$, $A_1$ is linear or branched alkyl having 1-6 carbon atoms or hydroxyalkyl having 1-4 carbon atoms, $R_8$, $R_9$ and $R_{10}$ each independently represents alkyl having 1-18 carbon atoms or benzyl, $R_5$ and $R_6$ represent hydrogen or alkyl having 1-6 carbon atoms and $X_1^\ominus$ represents chloride, bromide or methosulfate,

(11) polyalkylene imines,
(12) polymers containing vinyl pyridine or vinyl pyridinium units in the chain,
(13) condensates of polyamines and epichlorohydrin,
(14) quaternary polyureylenes and
(15) chitin derivatives.

3. The cosmetic composition of claim 1 wherein said vegetable oil is almond oil, peanut oil, wheat germ oil, lineseed oil, jojoba oil, oil of apricot pits, walnut oil, palm nut oil, pistachio nut oil, sesame seed oil, rape seed oil, cade oil, corn oil, peach pit oil, poppyseed oil, pine oil, castor oil, soybean oil, avocado oil, safflower oil, coconut oil, hazelnut oil, olive oil, grape seed oil or sunflower seed oil.

4. A process for conditioning the hair comprising at the time of conditioning the hair admixing the two separate liquid phases of the cosmetic composition of claim 13 so as to obtain a dispersion of the aqueous phase in the oily phase, applying 5 to 40 $cm^3$ of the resulting dispersion onto the hair, permitting said dispersion to remain in contact with the hair for at least 5 minutes and rinsing the hair.

5. The process of claim 4 wherein the rinsed hair is then shampooed.

6. A process for conditioning the skin comprising at the time of conditioning the skin admixing the two separate liquid phases of the cosmetic composition of claim 1 so as to obtain a dispersion of the aqueous phase in the oily phase, and applying an effective amount of the dispersion to the skin.

* * * * *